US007399445B2

(12) United States Patent
Kuroda et al.

(10) Patent No.: US 7,399,445 B2
(45) Date of Patent: Jul. 15, 2008

(54) CHEMICAL SENSOR

(75) Inventors: Ryo Kuroda, Kanagawa (JP);
Natsuhiko Mizutani, Tokyo (JP);
Takako Yamaguchi, Kanagawa (JP);
Yasuhisa Inao, Kanagawa (JP);
Tomohiro Yamada, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 565 days.

(21) Appl. No.: 10/340,152

(22) Filed: Jan. 10, 2003

(65) Prior Publication Data
US 2003/0132392 A1    Jul. 17, 2003

(30) Foreign Application Priority Data
Jan. 11, 2002   (JP)   ............... 2002-005017

(51) Int. Cl.
*C12Q 1/68*    (2006.01)
*G01N 1/02*    (2006.01)

(52) U.S. Cl. .................. 422/55; 422/50; 422/52; 422/57; 422/68.1; 422/82.05; 422/82.06; 422/82.07; 422/82.08; 422/82.09; 422/82.11; 422/83; 436/43; 436/63; 436/164; 436/171; 436/172; 356/300; 356/303; 356/310; 356/319; 356/328; 356/450

(58) Field of Classification Search .............. 422/50, 422/52, 55, 57, 68.1, 82.05, 82.06, 82.07, 422/82.08, 82.09, 82.11, 83; 436/43, 63, 436/164, 171, 172; 356/300, 303, 310, 319, 356/326, 450, 504, 328
See application file for complete search history.

(56) References Cited

U.S. PATENT DOCUMENTS 5,973,316 A * 10/1999 Ebbesen et al. ............. 250/216
5,994,150 A   11/1999 Challener et al. ........... 436/518
6,052,238 A    4/2000 Ebbesen et al. ............. 359/738
6,268,125 B1   7/2001 Perkins ......................... 435/5
6,277,653 B1   8/2001 Challener et al. ........... 436/518
6,432,364 B1   8/2002 Negami et al. ............ 422/82.11
6,653,152 B2  11/2003 Challener .................... 436/518

(Continued)

FOREIGN PATENT DOCUMENTS

JP    11-72607    3/1999

(Continued)

OTHER PUBLICATIONS

S. Linden et al., "Controlling the Interaction between Light and Gold Nanoparticles: Selective Suppression of Extinction," 86(20) *Phys. Rev. Lett.* 4688-91 (May 2001).

(Continued)

*Primary Examiner*—Brian J Sines
(74) *Attorney, Agent, or Firm*—Fitzpatrick, Cella, Harper & Scinto

(57) ABSTRACT

A sensor device is formed from a metal film having a plurality of openings, a sensor material positioned within each of the openings, a light source that emits light having a first wavelength, and a light detector that detects light emitted from the light source and transmitted through or reflected from the openings. The plurality of openings are arranged periodically in a first direction in the metal film, and both a size of each of the plurality of openings and an interval thereof in the first direction are equal to or less than the wavelength of the light.

16 Claims, 11 Drawing Sheets

U.S. PATENT DOCUMENTS

| | | | |
|---|---|---|---|
| 6,692,974 B2 | 2/2004 | Perkins | 436/518 |
| 6,818,907 B2 * | 11/2004 | Stark | 250/492.1 |
| 6,862,094 B2 | 3/2005 | Johansen | 356/445 |
| 7,008,794 B2 | 3/2006 | Goh et al. | 436/164 |
| 7,067,322 B2 * | 6/2006 | Corn et al. | 436/120 |
| 2003/0036204 A1 * | 2/2003 | Stark et al. | 436/172 |
| 2005/0062973 A1 * | 3/2005 | Kim et al. | 356/445 |

FOREIGN PATENT DOCUMENTS

| | | |
|---|---|---|
| JP | 2000-346845 | 12/2000 |
| JP | 2000-356587 | 12/2000 |
| JP | 2001-504582 | 4/2001 |
| JP | 2001-523819 | 11/2001 |
| WO | WO 01/40757 A2 | 6/2001 |
| WO | WO 01/69209 A1 | 9/2001 |
| WO | WO 01/71322 A2 | 9/2001 |

OTHER PUBLICATIONS

H.F. Ghaemi et al., "Surface Plasmons Enhance Transmission Through Subwavelength Holes," 58(11) *Phys. Rev.* B 6779-82 (Sep. 1998).

* cited by examiner

Fig. 5 (a)
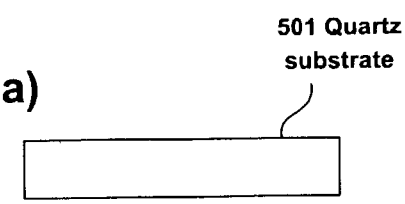
501 Quartz substrate
Fig. 5 (b)
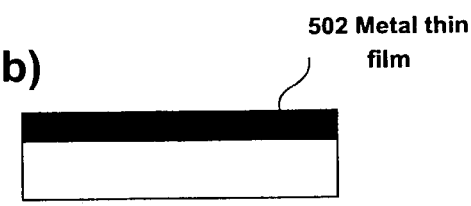
502 Metal thin film
Fig. 5 (c)
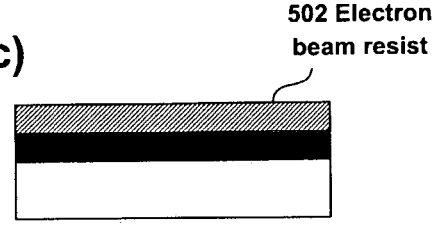
502 Electron beam resist
Fig. 5 (d)
Fig. 5 (e)
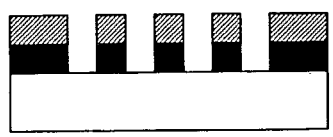
Fig. 5 (f)
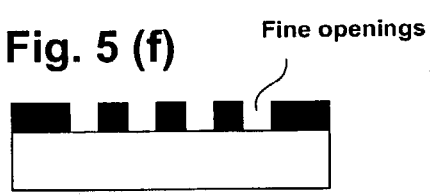
Fine openings
Fig. 5 (g)
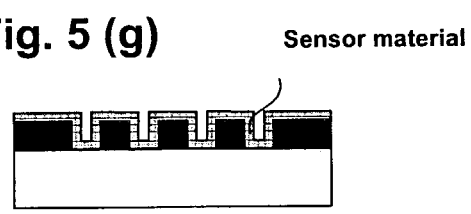
Sensor material
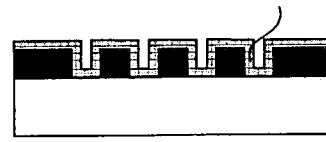

SEM image of 20-nm gold colloid monolayer

CHEMICAL SENSOR

BACKGROUND OF THE INVENTION

1. Field of the Invention

The present invention relates to chemical sensors, including biosensors, used in medical and health diagnoses and food testing.

2. Related Background Art

In recent years, the demand for medical diagnosis and food testing has been escalating, and the development of a compact, high-speed sensing, low-cost biosensors is sought. To this end, biosensors utilizing electrochemical methods with electrodes and FET have been made through an application of semiconductor processing technology.

However, further integration, lower cost and sensors compatible with any measuring environment are sought, and a biosensor that uses surface plasmon resonance as a transducer is considered promising to meet these demands. Such a biosensor would make use of surface plasmon resonance that is generated on a metallic thin film provided on the surface of total-reflection prism to detect whether a substance is adsorbed, such as whether an antigen is adsorbed in an antigen-antibody reaction.

Recently, a localized plasmon resonance sensor that uses metal fine particles has been proposed to achieve a highly sensitive sensing. In the localized plasmon resonance sensor, changes in the medium in vicinity of the metal fine particles are detected by irradiating a light on a substrate to which metal fine particles are fixed and measuring the absorbancy of the light transmitted through the metal fine particles.

In conventional localized plasmon resonance sensors that use metal fine particles, a film of metal fine particles is formed on a substrate by using a metal colloidal solution; however, this entails a difficulty in gaining a uniformity in the size of metal fine particles in the metal colloidal solution within a deviation of 10~20%. In addition, due to the fact that the substrate is simply immersed in the metal colloidal solution, the arrangement of the metal fine particles on the substrate is completely random, so that neither the interval between the metal fine particles nor the arrangement direction of the metal fine particles can be controlled.

As a result, the width of absorbancy spectrum in such sensors is wide, which lowers the peak intensity; this causes changes in signals that detect changes in the medium in the vicinity of the metal fine particles to be low, which in turn causes the sensitivity of the sensor to be limited.

SUMMARY OF THE INVENTION

The present invention relates to a sensor device comprising a metal film provided with a plurality of openings, a sensor material positioned within each opening, a light source, and a light detector that detects light emitted from the light source and transmitted through or reflected from the openings, wherein the openings are arranged periodically in a first direction within a surface of the metal film, and both the size and interval of the direction are less than or equal to the wavelength of the light.

Furthermore, the present invention relates to a sensor medium comprising a metal film provided with a plurality of openings and a sensor material positioned within each opening, wherein the openings are arranged periodically in a first direction within a surface of the metal film and both the size and interval of the direction are less than or equal to 200 nm.

Moreover, the present invention relates to a testing method, the method comprising the steps of bringing a sensor medium that consists of a metal film provided with a plurality of openings and a sensor material positioned within each opening into contact with a test subject, irradiating a light onto the sensor medium, and detecting the light that transmitted through or reflected from the openings, wherein the openings are arranged periodically in a first direction within a surface of the metal film and both the size and interval of the direction are less than or equal to the wavelength of the light.

Other features and advantages of the invention will be apparent from the following detailed description, taken in conjunction with the accompanying drawings that illustrate, by way of example, various features of embodiments of the invention.

BRIEF DESCRIPTION OF THE DRAWINGS

FIGS. 5(a)-5(g) show a method for manufacturing a sensor medium.

DESCRIPTION OF PREFERRED EMBODIMENTS

[Sensor Device and Sensor Medium]

A chemical sensor device includes a sensor material, which comes into contact with a test subject and reacts with a detection target, and a measuring equipment, which electrically, optically or through other methods measures changes in the sensor material before and after contact. Due to the fact that the sensor material may be exposed to the test subject at a distance from the measuring equipment part in some cases, the sensor material is carried on an appropriate carrier; the sensor material and its carrier together are called a sensor medium.

Figure 1:
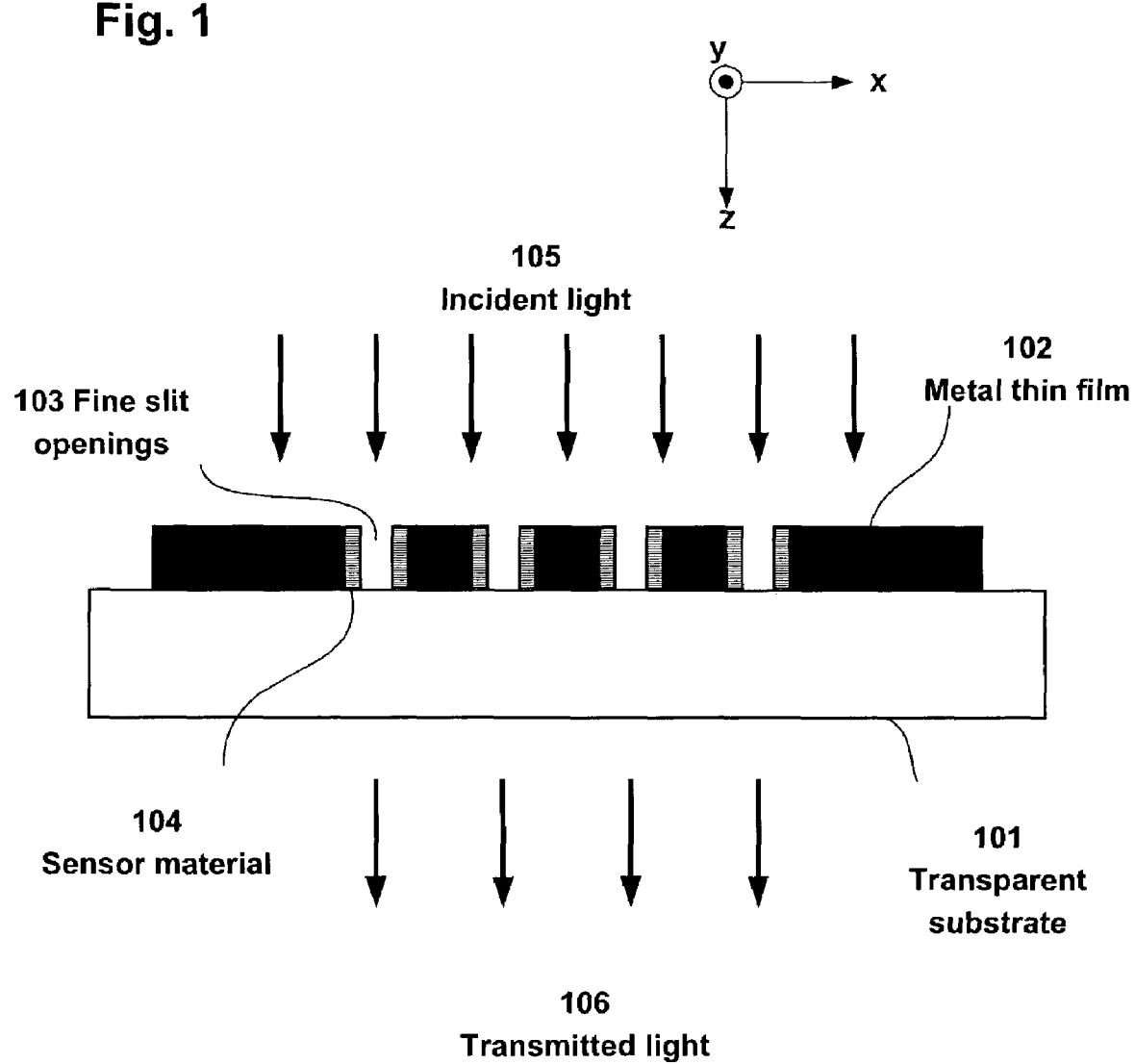
FIG. 1 is a drawing illustrating the configuration and detection principle of a sensor medium in accordance with the present invention.
Figure 2:
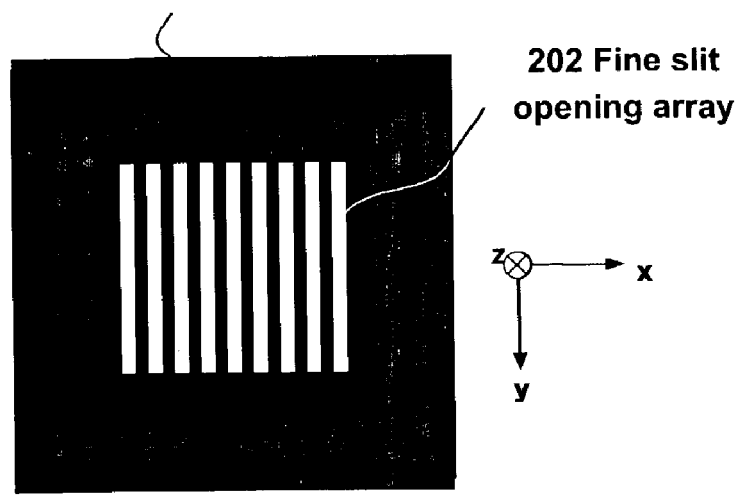
FIGS. 2(a)-2(c) are plan views of sensor media in accordance with the present invention.
Figure 2:
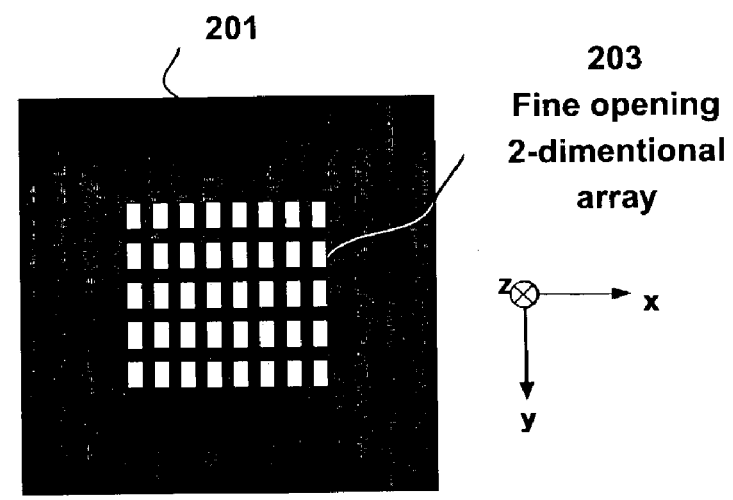
Figure 2:
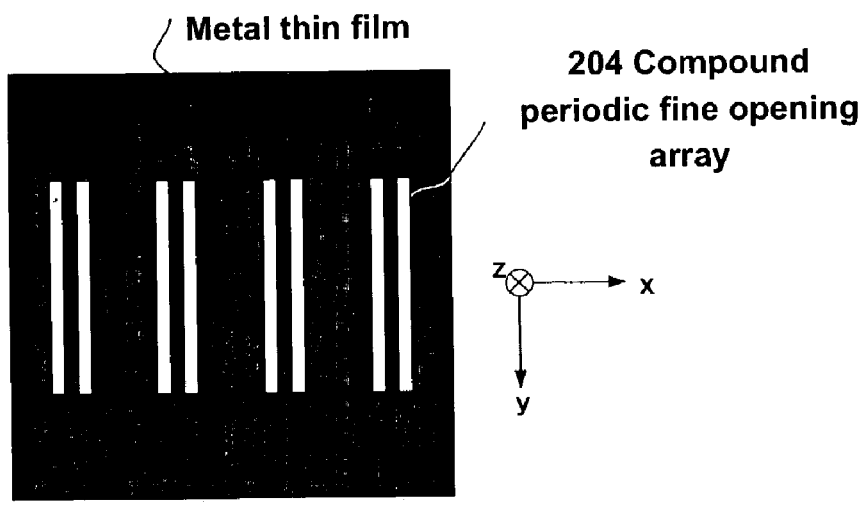

Referring to FIGS. 1 and 2, a sensor medium in a sensor device according to the present invention will be described.

FIG. 1 shows a cross section of a sensor medium in accordance with one embodiment of the present invention.

A sensor medium includes a transparent substrate 101, on top of which are provided a sensor material 104 and a metal thin film 102 with openings. In the metal thin film 102 are provided fine openings 103 arranged in one direction within the surface of the metal thin film 102, i.e., in the x direction in FIG. 1. The thickness of the metal thin film 102 is approximately 10 nm-500 nm.

FIG. 2(a) indicates a plan view of the fine slit openings arranged. In FIG. 2(a), a fine slit opening array 202 is formed arranged in the x direction in the metal thin film 201 in such a manner that the short side of each opening is arranged in the x direction, while the long side of each opening is arranged in the y direction. As shown in FIG. 2(a), each of the fine openings 103 is a slit-shaped opening in which its size in the y direction, which is orthogonal to the x direction within the surface of the metal thin film 102, is larger than its size in the x direction. The width in the x direction of each fine slit opening 103 is a predetermined value that can be selected from the range of about 1-200 nm, and the interval between adjacent fine slit openings 103, or the width of each metal part, is a predetermined value that can be selected from the range of about 1-200 nm.

On an inner surface of each fine slit opening 103 is provided the sensor material 104. When the sensor material 104 comes into contact with a test subject, the sensor material 104 fixes, through surface adsorption or chemical bonding, a detection target substance contained in the test subject. Alternatively, the sensor material 104 may be such that a part of its components dissociates and bonds with the detection target substance. In the present invention, the sensor material 104 may consist of a material whose optical properties, such as refraction index or absorption rate, change due to its bonding with the detection target substance or disassociation of a component of the sensor material 104.

[Operational Principle of Chemical Sensors]

Next, referring to FIGS. 1, 3 and 4, the operational principle of a chemical sensor according to the present invention will be described.

In FIG. 1, an incident light 105 enters the arrangement of the fine slit openings 103 downward from the top (in +z direction). Due to the fact that both the size and interval of the fine slit openings 103 are less than or equal to the wavelength of the light used for detection, components within the electric field of the incident light 105 that are deflected in the x direction in the figure interact with electrons within the metal thin film 102 and cause surface plasmon to be generated on the inner surface of the fine slit openings 103. The surface plasmon generated propagates downward (in +z direction) along the inner surface of each of the fine slit openings 103, becomes converted to light again at the bottom edge of each of the fine slit openings 103, and transmits downward (in +z direction) as a transmitted light 106.

When the light, as it undergoes a surface plasmon state, transmits through a plurality of fine slit openings 103, the light is absorbed by a resonance (localized plasmon resonance) with electric multipole that is generated in the fine slit openings 103; this causes the spectrum of wavelength changes of the incident light 105 to have a characteristic resonance peak. The shape of the localized plasmon resonance peak varies depending on the width and interval of the fine slit openings 103.

Due to the fact that, in the sensor medium according to the present invention, the fine slit openings 103 are arranged periodically, the width of the resonance peak is narrow and its height high. Further, due to the fact that the openings are slit-shaped, the resonance absorption between a dipole in the direction that transverses the slits and the incident light 105 becomes intensified. Consequently, by having the incident light 105 deflect in the direction that the direction of the electric field transverses the slits, the resonance peak can be made even sharper.

Figure 3:
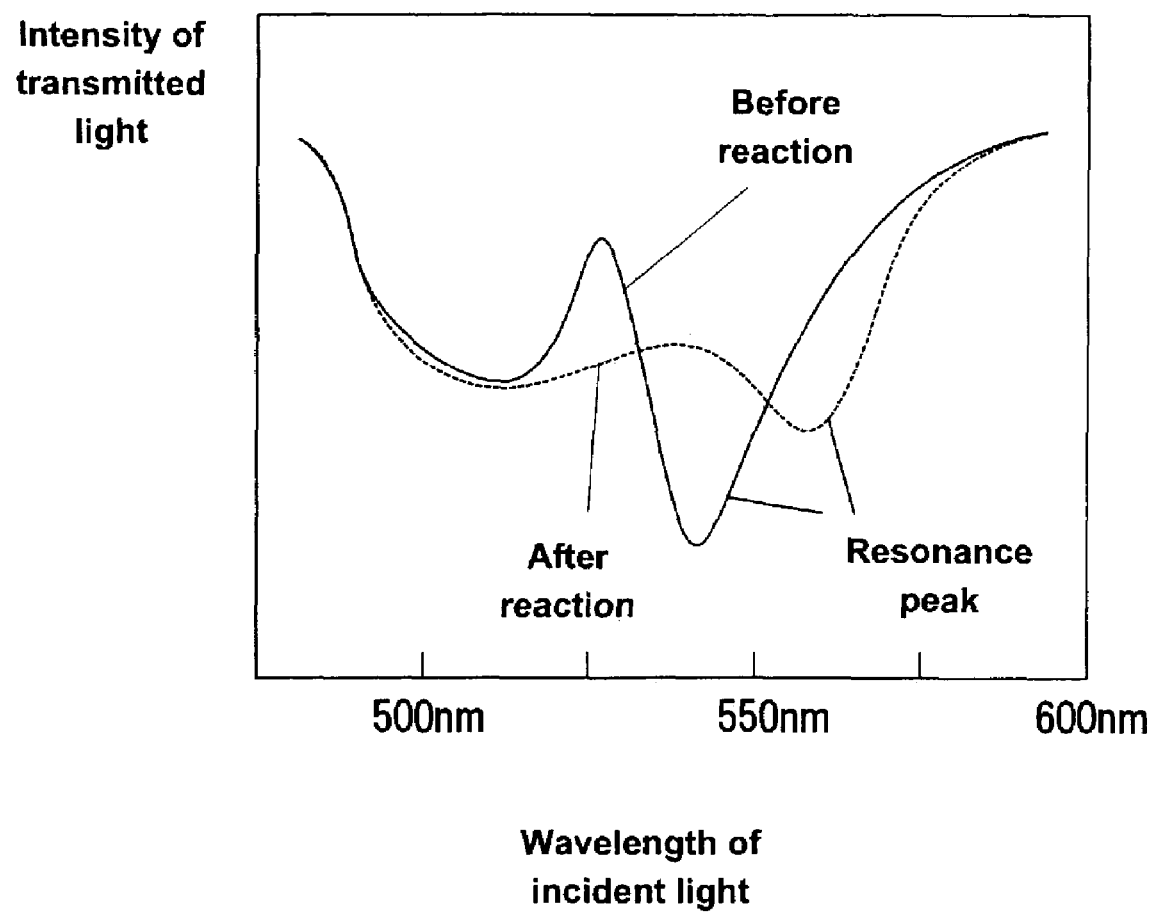
FIG. 3 is a graph showing changes in a transmitted light intensity spectra in the sensor medium according to the present invention.

The intensity spectrum of the transmitted light in the sensor medium according to the present invention is indicated by a solid line in FIG. 3. The solid line indicates the spectrum before the sensor material 104 reacts. The sensor medium shown in FIG. 1 comes into contact with a test subject such as a test solution or a test gas, and the sensor material 104 and the test subject react. The transmission spectrum after reaction is indicated by a broken line.

The reason for the changes in the spectrum through reaction is presumed to be the following:

When the sensor material 104 and a test subject react, the film thickness of the sensor material 104 inside each of the fine slit openings 103 increases slightly, which changes the combined average refraction index of the opening and the sensor material 104 in each of the fine slit openings 103. The change in the refraction index causes an equivalent change in the width of the opening, which in turn changes the position and height of the resonance peak; consequently, the shape of the intensity spectrum of the transmitted light changes, as shown in a graph as an example in FIG. 3.

By detecting the change in the position and height of the resonance peak, the detection sensitivity of the sensor becomes significantly enhanced. As a result, although the sensor device in accordance with the embodiment of the present invention may use a single wavelength light to measure only changes in intensity, a more preferable sensor device may use a light source that emits a light within a certain range of wavelengths somewhat shorter and longer than the wavelength of the resonance peak, in order to perform detection with a sensor that includes a spectrometer.

An example of the sensor material 104 that would have the reaction described above may be: (1) an antibody substance that forms a specific bond with an antigen substance contained in a test subject, which allows a change in refraction index inside the fine slit openings 103 before and after the bonding to be detected; or, (2) a complex of measurement target-like substance contained in a test subject and an enzyme, wherein an antigen that is the measurement target substance is brought into contact with the complex, whereby the complex disassociates and an antigen-antibody complex of the enzyme and the measurement target substance forms. In this case, a change can be detected in the refraction index inside the fine slit openings 103 before and after reaction. In other words, as the sensor material 104, a substance that can detect a change in the refraction index inside the fine slit openings 103 before and after the dissociation-and-bonding process, can be used.

Alternatively, changes in absorption spectrum or fluorescent spectrum that occur as a result of the sensor material 104 inside the fine slit openings 103 reacting with a test subject may be detected. In these cases as well, there is an electric field reinforcement effect that takes place inside the fine slit openings 103 due to the surface plasmon, which causes the sensor material 104 to be excited by an electric field ten to a thousand times stronger than the electric field of the incident light 105; consequently, the absorption and fluorescent intensity become larger, which significantly enhances the detection sensitivity of the sensor.

A specific example of the sensor material 104 that would have the reaction described above may be: (3) an antibody substance that forms a specific bond with an antigen substance contained in a test subject, which allows a change in fluorescence or absorption of a labeled substance before and after the bonding to be detected; or, (4) a complex of a measurement target-like substance contained in a test subject and a labeled enzyme, wherein an antigen that is the measurement target substance is brought into contact with the complex, whereby the complex disassociates and an antigen-antibody complex of the labeled enzyme and the measurement target substance forms. A change in the fluorescence generated inside the fine slit openings 103, or a change in the absorption caused by materials inside the slits, before and after reaction, can be detected. In other words, as the sensor material 104, a substance that can detect a change in fluorescence or absorption accompanying a change in the labeled enzyme before and after the dissociation-and-bonding process, can be used.

The above example detects light that transmits through fine slit openings 103, but the concept of the present invention is not limited to this and a configuration that detects a reflected light of an incoming light entering the fine slit openings 103 may also be used. However, due to the fact that detecting transmitted light in effect detects light that has transmitted through the fine slit openings 103, stray light is less likely to affect this configuration, which has an effect of improving the S/N ratio of signal intensity, than a configuration that detects reflected light.

Instead of the fine slit openings 103 shown in FIG. 2(a), a fine opening two-dimensional array 203, in which the openings are periodically arranged in the y direction also, shown in FIG. 2(b) can be used. Both the size and interval in the y direction are set to be less than or equal to the wavelength of the light irradiated. In this case, sensor information can be independently and simultaneously obtained concerning an incoming light that has deflection in the x direction, as well as in the y direction.

Alternatively, a compound periodic fine opening array 204, which consists of a compound periodic structure comprising two or more periods, as shown in FIG. 2(c) can be used. For example, by arranging sets of two fine opening arrays, the mode of plasmon excited between three or more fine openings can be restrained, which can reduce the excitation plasmon mode. Although this example indicates a structure in which sets of two fine opening slits are arranged periodically, there can be sets of three, four, etc., or sets of two fine opening slits, two fine opening slits, three fine opening slits that forms a triple, quadruple, etc. compound periodic structure. Since the excitation plasmon mode can be controlled by modifying the design of the periodic structure in this way, the shapes of specific wavelengths' peaks can be controlled, which makes it possible to select a range of wavelengths optimal as a detection light depending on the sensor material 104.

Embodiment 1

Figure 4:
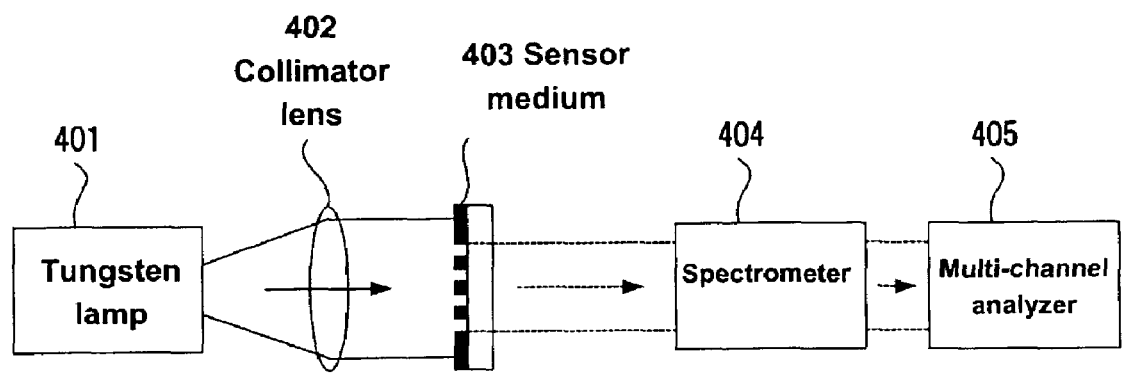
FIG. 4 schematically shows a configuration of a specific sensor device using the sensor medium according to the present invention.

A exemplary device configuration of a sensor device that uses a sensor medium in accordance with an embodiment of the present invention is shown in FIG. 4. In this example, a white light from a tungsten lamp 401 is collimated into virtually parallel lights by a collimating lens 402, and the lights enter a sensor medium 403. The lights that have transmitted through the sensor medium 403 enter a spectrometer 404, the spectrally resolved lights are detected by a multi-channel analyzer 405, and spectrum information is obtained.

A material for the metal thin film (102 in FIG. 1) of the sensor medium is selected from among metals in general, but gold, silver, copper and aluminum especially generate large surface plasmon and are therefore desirable in the present invention. In particular, gold has a peak caused by localized plasmon resonance in the entire visible region and is consequently ideal to constitute a sensor that uses visible light for detection. In addition, by using an alloy of gold, silver, copper and aluminum in predetermined composition ratios, the position of the peak can be adjusted anywhere between near-ultraviolet region and near-infrared region.

The sensor material (104 in FIG. 1) can be any substance that, when it reacts with a test subject, causes changes in film thickness, refraction index, absorption spectrum or fluorescent spectrum; materials used in chemical sensors, including such biosensors as enzyme sensors, microbial sensors, organelle sensors, tissue sensors, immunity sensors, enzyme immunity sensors and bio-affinity sensors, can be used as the sensor material.

Figure 6:
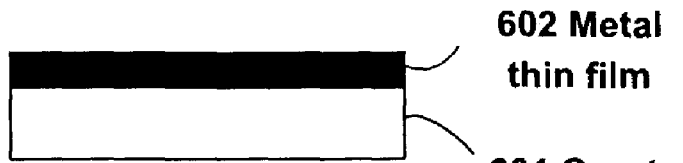
FIGS. 6(a)-6(e) show a nano-molding method as part of the method for manufacturing the sensor medium.
Figure 6:
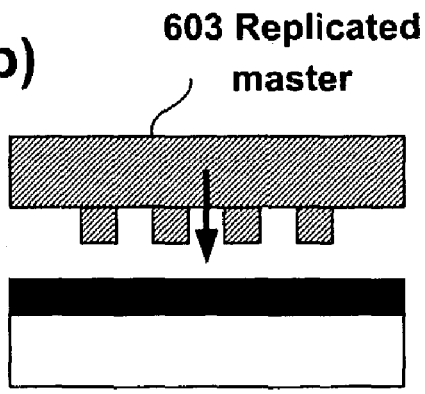
Figure 6:
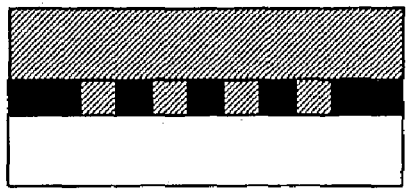
Figure 6:
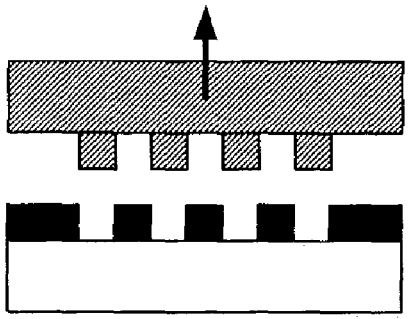
Figure 6:

Referring to FIGS. 5 and 6, a method for manufacturing the sensor medium will be described.

A metal thin film 502 is formed to a film thickness of 50 nm on a quartz substrate 501 using the sputtering method (FIG. 5(b)). On top of the metal thin film 502, an electron beam resist 503 is formed to a film thickness of 10 nm through spin coating, exposed by an electron beam drawing apparatus, and, after developing, an L/S=20 nm/20 nm resist pattern is obtained (FIG. 5(d)). Next, the metal thin film 502 is etched (FIG. 5(e)) using the resist pattern as a mask, and then the resist is removed whereby fine openings 504, each having an opening width of 20 nm at an interval of 20 nm, are formed (FIG. 5(f)). After rendering a surface treatment on the metal thin film 502, a sensor material 505 is allowed to bond with the metal thin film 502 (FIG. 5(g)). When this happens, the sensor material 505 bonds not only on the inside of each of the fine openings 504, but also on the surface of the metal thin film 502. However, due to the fact that the surface is not directly related to the detection principle of the sensor according to the present invention, it can be used in this state.

Although the manufacturing method for fine opening patterns using an electron beam drawing apparatus has been described, various types of scanning probe machining devices, x-ray exposure devices, EUV exposure devices and electron beam steppers that apply principles of focused ion beam machining devices, scanning-tunneling microscopes, atomic force microscopes and near-field optical microscopes can be used for manufacture.

A simple and low-cost sensor medium can be manufactured by using an exposure device that makes use of near-field light, or a nano-molding method shown in FIG. 6. In FIG. 6, a metal thin film 602 is formed to a thickness of 50 nm on a quartz substrate 601 (FIG. 6(a)). After pressure bonding a replicated master 603, in which an L/S=20 nm/20 nm pattern is formed on a SiC surface using an electron beam drawing apparatus, on the surface of the metal thin film 602 by applying a load (FIG. 6(b), FIG. 6(c)), the replicated master 603 is removed (FIG. 6(d)), and fine openings 604 are formed (FIG. 6(e)).

Embodiment 2: Multi-Channeling

Figure 7:
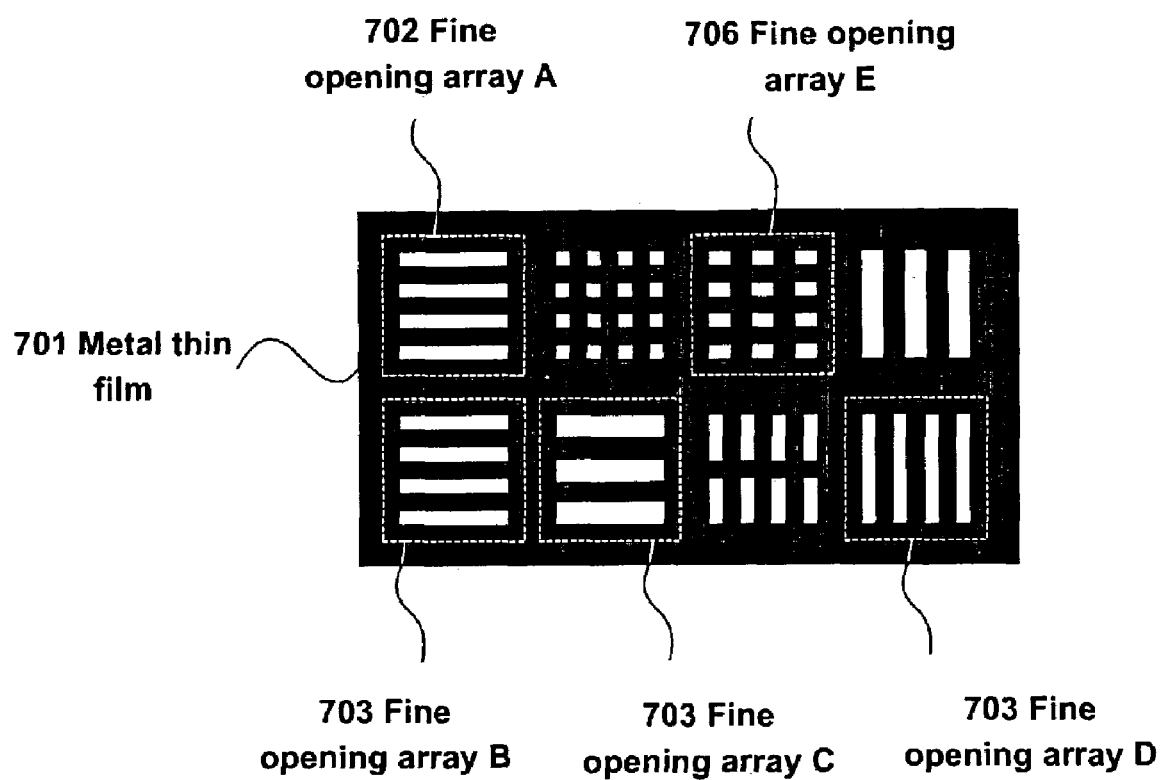
FIG. 7 shows a plan view of a multi-channel sensor medium.

FIG. 7 indicates a multi-channel sensor medium, in which a plurality of slits and two-dimensional fine opening arrays 702-706 are provided in a metal thin film 701, as a sensor medium in accordance with an embodiment of the present invention.

Figure 8:
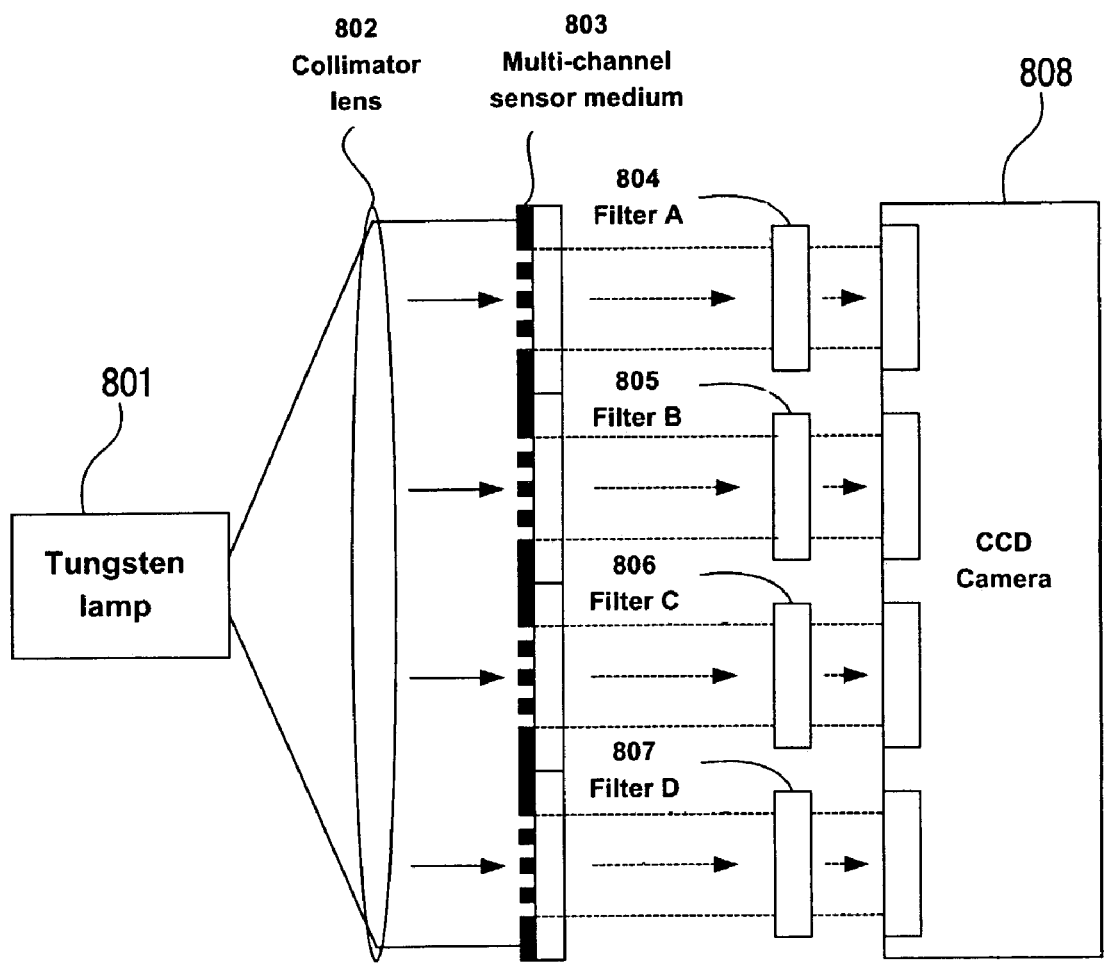
FIG. 8 shows a configuration of a multi-channel sensor device.

The configuration of a multi-channel sensor device consisting of the multi-channel sensor medium is shown in FIG. 8. A light from a tungsten lamp 801 is collimated into virtually parallel lights by a collimating lens 802, and the lights enter a multi-channel sensor medium 803. A plurality of transmitted lights that transmitted through various fine opening arrays of the multi-channel sensor medium 803 go through filters A (804)-D (807), enter a CCD camera 808, and their transmission pattern information is obtained.

Through this process, relative spectrum information not dependent on the intensity of irradiated light can be obtained by having lights that passed through the same pattern, such as the fine opening array A (702) and the fine opening array B (703) in FIG. 7, pass through bandpass filters of different wavelengths and by comparing the lights that come through the filters. Similarly using the same pattern, such as the fine opening array A (702) and the fine opening array B (703), sensor materials of different types can be provided on the inside of the openings of the two arrays and lights that passed through respective fine opening arrays can be independently detected in order to simultaneously obtain a plurality of sensing information. Further, by making a relative comparison of such information, a highly sensitive detection through differential detection becomes possible. In addition, by making comparisons between patterns with differing fine opening pitches and/or arrangement directions and two-dimensional patterns, different information can be simultaneously obtained. By using patterns with differing fine opening pitches and/or sizes and changing the signal peak position, a spectrum region in which to detect signals can be freely selected. This makes it possible to detect in a plurality of light wavelengths, so that even when a multi-channel sensor medium is compactly integrated as in the present embodiment, signal separation can be easily done by using an interference filter. Furthermore, in the type of sensors that detects fluorescent spectrum or absorption spectrum, the spectrum region in which to detect signals can be freely selected by using patterns with differing fine opening pitches and/or sizes to change the signal peak position; consequently, the range of sensor material selection becomes wider and application to wider areas becomes possible.

Embodiment 3

Figure 9:
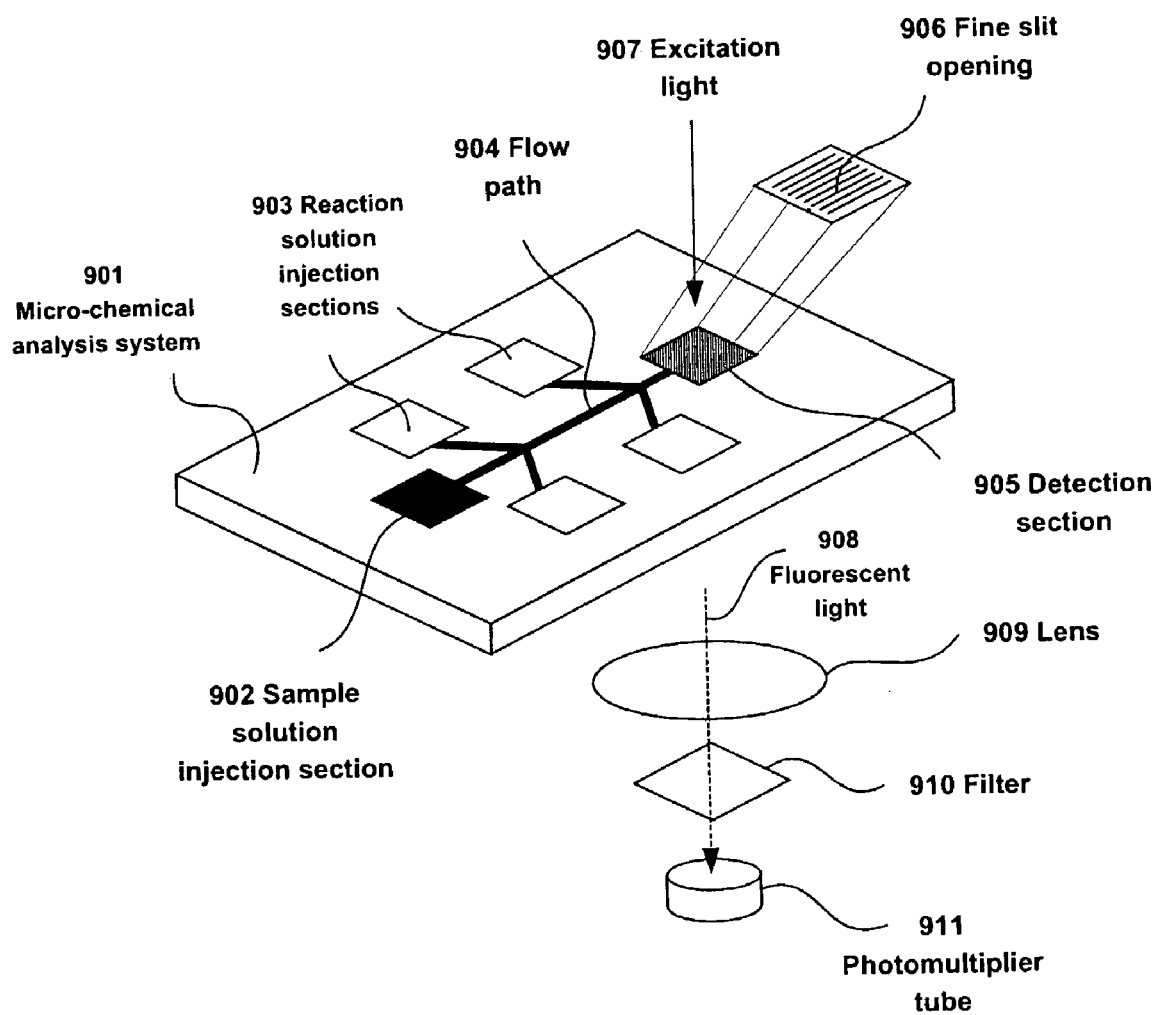
FIG. 9 shows an example in which the sensor medium according to the present invention is formed in a unitary fashion with a micro-chemical analysis system.

FIG. 9 is an example in which a sensor medium in accordance with an embodiment of the present invention is formed in a unitary fashion with a micro-chemical analysis system (called μ-TAS: micro-total analysis system or lab-on-a-chip).

In a micro-chemical analysis system 901 in FIG. 9, a test solution injected into a sample solution injection section 902 passes through a flow path 904, reacts with a reaction solution injected into reaction solution injection sections 903, and reaches a detection section 905. As shown in an enlargement in the figure, fine slit openings 906 are provided in the detection section 905 for detection based on the principle of the present invention. The test solution seeps into the interior of the fine slit openings 906 and reacts with a sensor material inside the fine slit openings 906. An excitation light 907 is irradiated on the detection section 905; fluorescent lights 908 emitted from the fine slit openings 906 converge on a lens 909; the converged light passes through a filter 910; and the light is detected on a photomultiplier tube 911.

Figure 10:
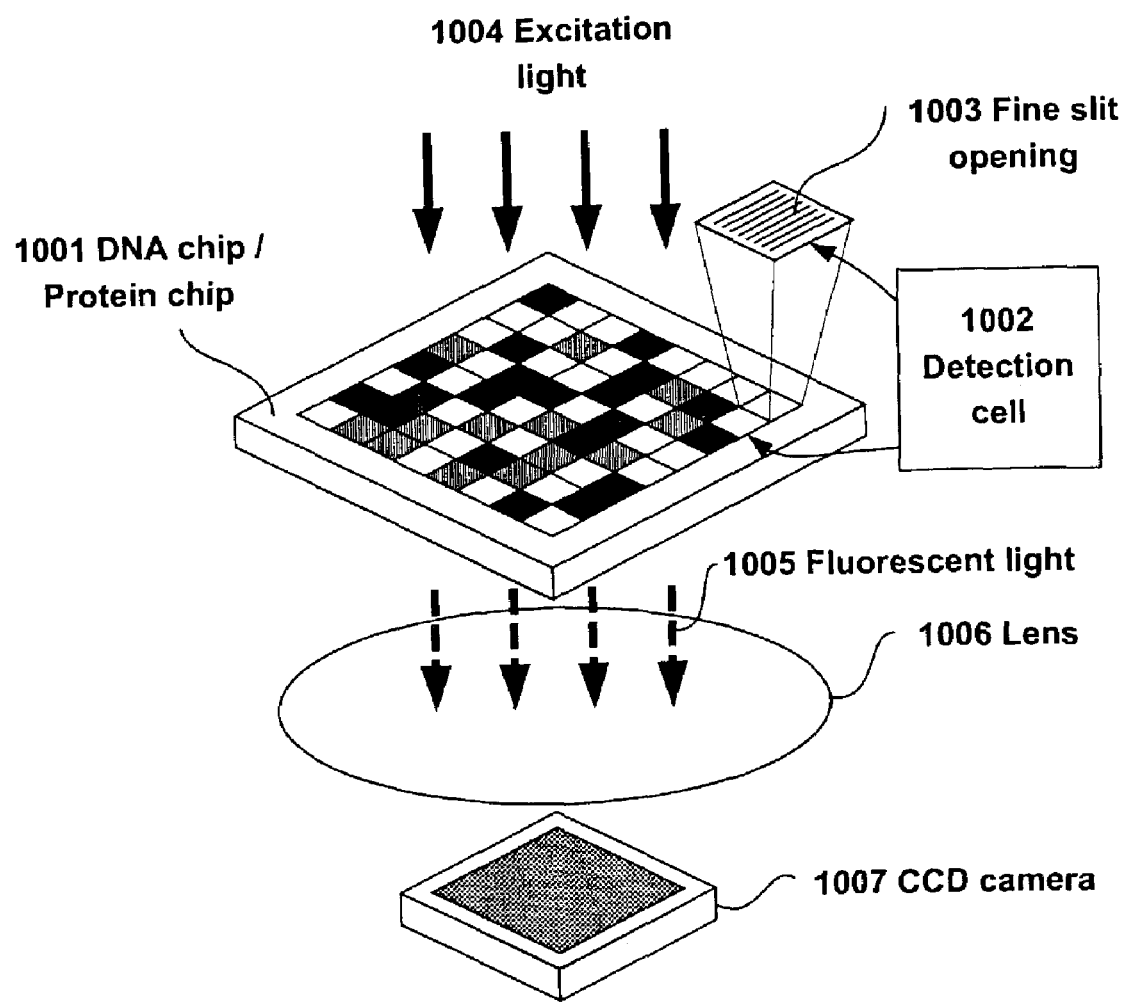
FIG. 10 shows an example in which the sensor medium according to the present invention is formed in a unitary fashion with a DNA chip or a protein chip.
Figure 11:
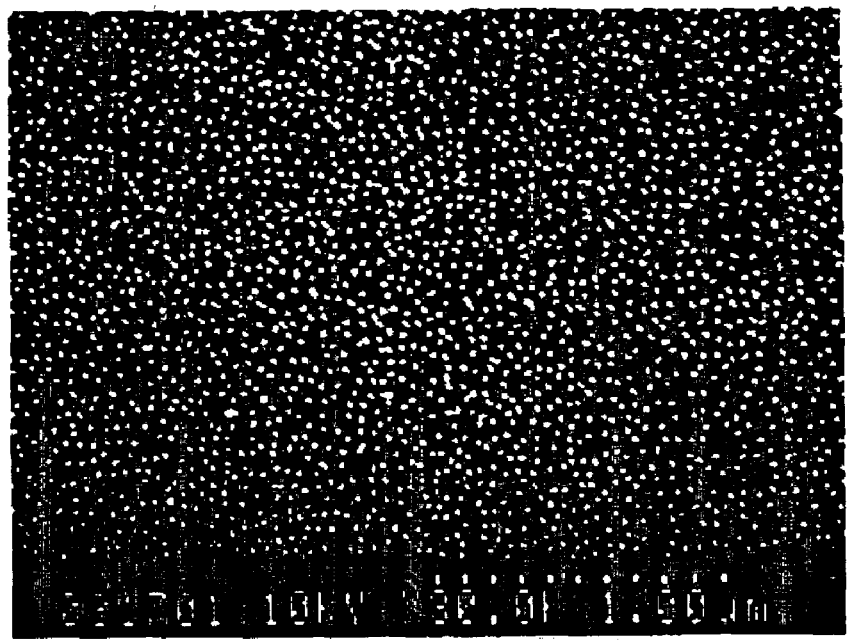
FIG. 11 shows an SEM image of an example of conventional colloid monolayer.

FIG. 10 is an example in which a sensor medium according to the present invention is formed in a unitary fashion with a DNA chip or a protein chip.

In each detection cell 1002 of a DNA chip/protein chip 1001 in FIG. 10, fine slit openings 1003 are provided and a sensor material is provided on the inner surface of each of the fine slit openings 1003. An excitation light 1004 is irradiated on the fine slit openings 1003; patterns of fluorescent lights 1005 emitted from various detection cells 1002 are focused on a CCD camera 1007 using a lens 1006; and pattern information is obtained.

The sensor media according to the present invention can be used by combining them with various types of sensors, which enhances signal intensity and makes possible detection with higher sensitivity.

As described above, according to the present invention, by providing a sensor material inside fine openings arranged at a period of width less than or equal to 200 nm at an interval of less than or equal to 200 nm, highly sensitive chemical sensors with narrow localized plasmon resonance spectrum width and high peak intensity, as well as highly sensitive chemical sensors with large absorption spectrum or fluorescent spectrum intensity, can be realized.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A sensor device for detecting a target substance by utilizing a localized plasmon resonance in a sensor medium, comprising:

a sensor medium comprising a substrate, a metal film having a plurality of slit openings formed on the substrate, and a sensor material for fixing a target substance positioned within the slit openings, the sensor material being capable of changing its optical properties by reacting with the target substance;

a light source unit that irradiates polarized light having a wavelength toward the sensor medium;

a light detector that detects light transmitted through or reflected from the sensor medium; and a measuring unit that measures a change of a spectrum or an intensity of light detected by the light detector, wherein the plurality of slit openings are arranged periodically in a first direction in the metal film, a length of each of the plurality of slit openings in the first direction and an interval between the slit openings in the first direction are equal to or less than the wavelength of the light, wherein each of the plurality of slit openings extends in a second direction orthogonal to the first direction and has a length in the second direction that is greater than the length in the first direction, and wherein the localized plasmon resonance generated in the sensor medium by the polarized light having an electric field parallel to the first direction causes the change of the spectrum or the intensity of light detected by the light detector, and the target substance is detected based on the change.

2. A sensor device according to claim 1, wherein the plurality of slit openings are arranged periodically in the second direction in the metal film, and the length of each of the plurality of slit openings in the second direction and an interval between the slit openings in the second direction are less than or equal to the wavelength of the light.

3. A sensor device according to claim 1, wherein the metal film is composed of a single metal of gold, silver, copper or aluminum, or an alloy of gold, silver, copper and aluminum.

4. A sensor device according to claim 1, wherein the sensor material is a chemical sensor material.

5. A sensor device according to claim 1, wherein the sensor material is a biosensor material.

6. A sensor device according to claim 1, wherein the substrate is transparent to a wavelength region including a wavelength of the light emitted from the light source, and the light detector detects the light transmitted through the sensor medium.

7. A sensor device according to claim 6, wherein the substrate is a quartz substrate.

8. A sensor device according to claim 1, wherein the light detector includes a spectrometer.

9. A sensor device according to claim 1, wherein the plurality of slit openings are arranged in a plurality of sets, and a length of each of the plurality of slit openings and/or an interval between the slit openings in one of the plurality of sets are different from a length of each of the plurality of slit openings and/or an interval between the slit openings in another of the plurality of sets.

10. A sensor device according to claim 9, wherein the light detector detects light transmitted through or reflected from the sensor medium independently for each of the plurality of sets.

11. A sensor device according to claim 1, wherein the plurality of slit openings are arranged in a plurality of sets in the metal film, and a length of each of the plurality of slit openings and/or an interval between the slit openings in all of the plurality of sets are the same, wherein the light detector detects light transmitted through or reflected from the sensor medium independently for each of the plurality of sets and passing through a bandpass filter of a wavelength different for each of the plurality of sets.

12. A sensor device according to claim 1, wherein the plurality of slit openings are arranged in a plurality of sets in the metal film, a length of each of the plurality of slit openings and/or an interval between the slit openings in all of the plurality of sets are the same, and a different sensor material is disposed in each of the plurality of sets, wherein the light detector detects light transmitted through or reflected from the sensor medium independently for each of the plurality of sets.

13. A sensor device according to claim 1, wherein the metal film and the plurality of slit openings are formed integrally with a micro-chemical analysis system that is manufactured by using a semiconductor process.

14. A sensor device according to claim 1, wherein the metal film and the plurality of slit openings are formed integrally with a DNA chip that is manufactured by using a semiconductor process.

15. A sensor device according to claim 1, wherein the metal film and the plurality of slit openings are formed integrally with a protein chip that is manufactured by using a semiconductor process.

16. A testing method for detecting a target substance by utilizing a localized plasmon resonance in a sensor medium, comprising the steps of:
  preparing a sensor medium comprising a substrate, a metal film having a plurality of slit openings formed on the substrate and a sensor material for fixing the target substance positioned within the slit openings, the sensor material being capable of changing its optical properties by reacting with the target substance;
  bringing the sensor medium into contact with a test subject containing the target substance;
  irradiating polarized light onto the sensor medium and detecting the light that transmitted through or reflected from the sensor medium; and
  measuring a change of a spectrum or an intensity of the detected light before and after contact for detecting the target substance,
  wherein the plurality of slit openings are arranged periodically in a first direction in the metal film, a length of each of the plurality of slit openings in the first direction and an interval between the slit openings in the first direction are equal to or less than the wavelength of the light,
  wherein each of the plurality of slit openings extends in a second direction orthogonal to the first direction and has a length in the second direction that is greater than the length in the first direction, and
  wherein the localized plasmon resonance generated in the sensor medium by the polarized light having an electric field parallel to the first direction causes the change of the spectrum or the intensity of detected light, and the target substance is detected based on the change.

* * * * *

UNITED STATES PATENT AND TRADEMARK OFFICE
CERTIFICATE OF CORRECTION

| | | |
|---|---|---|
| PATENT NO. | : 7,399,445 B2 | Page 1 of 1 |
| APPLICATION NO. | : 10/340152 | |
| DATED | : July 15, 2008 | |
| INVENTOR(S) | : Ryo Kuroda et al. | |

It is certified that error appears in the above-identified patent and that said Letters Patent is hereby corrected as shown below:

COLUMN 1

Line 11, "a" should be deleted.

COLUMN 2

Line 4, "transmitted" should read --is transmitted--.

COLUMN 5

Line 51, "A" should read --An--.

COLUMN 6

Line 64, "transmitted" (second occurrence) should read --are transmitted--; and
Line 65, "go" should read --pass--.

Signed and Sealed this

Sixteenth Day of December, 2008

JON W. DUDAS
*Director of the United States Patent and Trademark Office*